United States Patent [19]

Ifuku et al.

[11] Patent Number: 5,734,046
[45] Date of Patent: Mar. 31, 1998

[54] METHOD FOR MANUFACTURING LIMONOID GLUCOSIDES

[75] Inventors: Yasushi Ifuku, Wakayama; Hisao Maeda, Osaka; Masaki Miyake, Wakayama; Nobuya Inaba, Wakayama; Shigeru Ayano, Wakayama; Yoshihiko Ozaki, Wakayama; Kazuyuki Maruyama, Kainan, all of Japan; Shin Hasegawa, Albany, Calif.

[73] Assignee: The United States of America as represented by the Secretary of Agriculture, Washington, D.C.

[21] Appl. No.: 595,607

[22] Filed: Feb. 2, 1996

[30] Foreign Application Priority Data

Oct. 17, 1995 [JP] Japan .................... 7-268492

[51] Int. Cl.$^6$ .............. C07H 1/00; C07H 15/24; C07G 17/00
[52] U.S. Cl. .............. 536/124; 536/128; 536/18.1
[58] Field of Search .............. 536/124, 128, 536/18.1

[56] References Cited

U.S. PATENT DOCUMENTS 5,041,425  8/1991  Hasegawa et al. .............. 536/18.1

FOREIGN PATENT DOCUMENTS 6-113871  10/1992  Japan .

*Primary Examiner*—John Kight
*Assistant Examiner*—Everett White
*Attorney, Agent, or Firm*—M. Howard Silverstein; John D. Fado; Margaret A. Connor

[57] ABSTRACT

A method for manufacturing limonoid glucosides that is superior in terms of industrial productivity is described. The method includes a step in which a raw material composed of citrus juice and/or molasses is passed through a flow passage equipped with an adsorbent having limonoid glucoside adsorptivity, after which the limonoid glucosides that have been adsorbed by the adsorbent in the flow passage are eluted into a solvent using a solvent capable of dissolving the limonoid glucosides, which yields a liquid containing limonoid glucosides.

3 Claims, 3 Drawing Sheets

METHOD FOR MANUFACTURING LIMONOID GLUCOSIDES

BACKGROUND OF THE INVENTION

1. Field of the Invention

The present invention relates to a method for manufacturing limonoid glucosides contained in citrus fruit and having excellent physiological activity.

2. Prior Art

Limonoid glucosides are a natural substance first reported in 1989, and are not being produced industrially at the present time despite the fact that they have excellent biological activity, such as antifeedant activity against insects and anti-cancer activity in laboratory animals.

In view of this, the following method for recovering limonoid glucosides from citrus fruit has already been proposed by the inventors of the present invention (see Japanese Laid-Open Patent Application 6-113871). With this method, the strained pulp produced in the juicing of citrus fruit is used as the recovery source. This strained pulp is first subjected to enzyme treatment by a batch method, after which limonoid glucosides are recovered from the extract obtained in this enzyme treatment. Specifically, the advantage of this method was that it allowed useful limonoid glucosides to be recovered from the strained pulp of citrus fruits that in the past would have been discarded.

However, although this method is advantageous in terms of resource conservation in that it makes use of the above-mentioned strained pulp that would otherwise be discarded, the enzyme treatment takes a long time (16 to 24 hours) in the recovery of the limonoid glucosides, and furthermore the disposal of the extraction residue is difficult, which means that this method is not suited to industrial mass production.

SUMMARY OF THE INVENTION

An object of the present invention is to offer a method for manufacturing limonoid glucosides that is superior in terms of industrial productivity.

The manufacturing methods in claims 1 to 2 allowed limonoid glucosides to be manufactured efficiently in an industrial setting and do not require any filtration or other pretreatment of a juice or molasses containing impurity solids, so production efficiency is better.

The manufacturing method in claim 3 allowed limonoid glucosides to be refined without any loss of limonoid glucosides.

Figure 1:
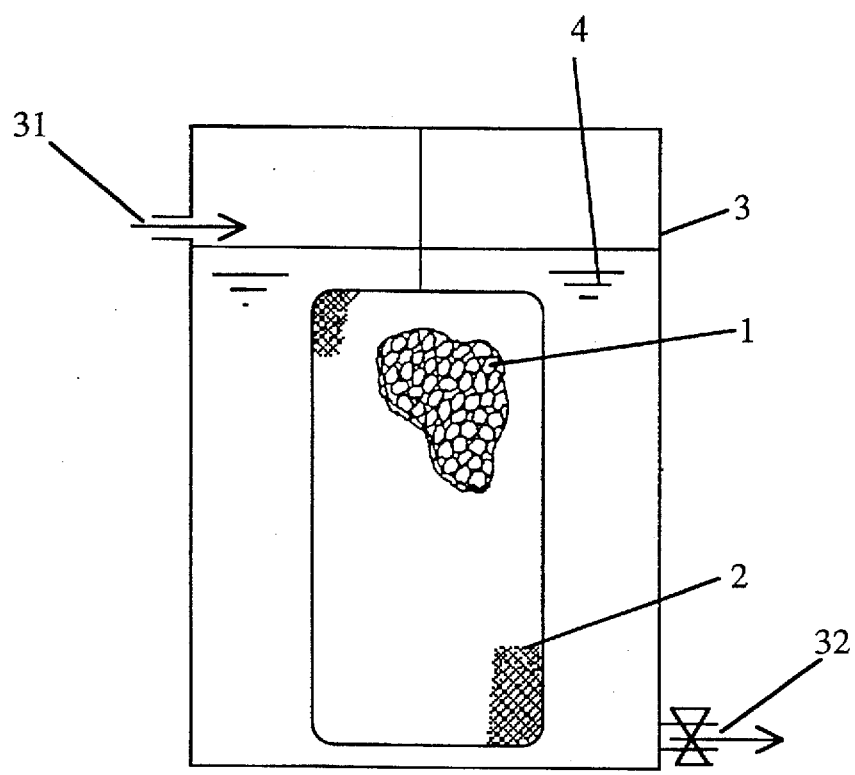
FIG. 1 is a diagram illustrating an example of the limonoid glucoside manufacturing method pertaining to the present invention.

Key: (1) adsorbent, (2) bag, (3) treatment tank (flow passage), (4) treatment liquid (raw material), (5) module (flow passage), (6) column (narrow passage), (7) adsorbent.

DETAILED DESCRIPTION OF THE INVENTION

In order to achieve the stated object, the limonoid glucoside manufacturing method pertaining to the invention in claims 1 or 2 comprises a step in which a raw material composed of citrus juice and/or molasses is passed through a flow passage equipped with an adsorbent having limonoid glucoside adsorptivity, after which the limonoid glucosides that have been adsorbed by the adsorbent in the flow passage are eluted into a solvent by means of a solvent capable of dissolving the limonoid glucosides, which yields a liquid containing limonoid glucosides.

Meanwhile, the limonoid glucoside manufacturing method pertaining to the invention in claim 1 additionally involves putting the adsorbent having limonoid glucoside adsorptivity into a bag having numerous liquid passage holes with a diameter smaller than the particle diameter of the adsorbent, and placing this bag along the flow passage.

The limonoid glucoside manufacturing method pertaining to the invention in claim 2 additionally involves passing citrus juice or molasses thereof through a flow passage at least part of which has been formed into a narrow passage in which an adsorbent having limonoid glucoside adsorptivity has been bonded and integrated along the inner walls.

The limonoid glucoside manufacturing method pertaining to the invention can involve exposing a liquid containing limonoid glucosides obtained by any of the manufacturing methods in claims 1 through 2 to an adsorbent that has no limonoid glucoside adsorptivity but is capable of removing impurity coloring components and unpleasant odor components, and the impurity coloring components and unpleasant odor components are thereby removed.

The limonoid glucoside manufacturing method pertaining to the invention in claim 3 involves supplying super-critical carbon dioxide under pressure to a liquid containing limonoid glucosides obtained by any of the manufacturing methods in claims 1 through 2, and unpleasant odor components and unwanted flavor components are thereby removed.

The citrus juice referred to in the above structure is not limited to juice obtained by the primary or secondary juicing of citrus fruit, and also encompasses the juice called peel water that is obtained in the secondary juice manufacturing process. "Molasses" refers to concentrated peel water. Also, juice is usually in the form of natural juice or concentrated juice, either of which may serve as the recovery source.

When a column method is to be used for treatment, the concentrated juice or molasses should be diluted first.

In the treatment, as much of the insoluble solids as possible should be removed from all of the raw materials by centrifugation or another such treatment. Specifically, if a raw material containing a large quantity of impurity solids is passed through a column that is tightly packed with an adsorbent, there is the danger that these impurity solids will adhere to the adsorbent surface and clog the column.

There are no particular restrictions on the adsorbent, but examples include XAD-2 (made by Organo), HP-20 (made by Mitsubishi Kasei), XUS (made by Dow Chemical), and other styrene DVB-based resin adsorbents, acrylic DVB-based resin adsorbents, styrene DVB-based (WA-30, made by Mitsubishi Kasei) and acrylic DVB-based (WA-10, made by Mitsubishi Kasei) anion exchange resins, completely porous substrate synthetic resins (such as Toyopearl, made by Tosoh), coconut shell activated charcoal (such as chromatograph-use activated carbon made by Wako Pure Chemical; average particle diameter 180 μm) and other such activated carbon, and chemically bonded silica gel (such as Chromatorex ODS DM1020T). The above adsorbents may be used singly or in combinations.

There are no particular restrictions on the solvent capable of dissolving limonoid glucosides, but methanol, ethanol, isopropyl alcohol, and other such alcohol-based solvents are suitable. There are no particular restrictions on the concentration of these solvents, but 50% or higher is preferable.

There are no particular restrictions on the bag used in the manufacturing method in claim 1, but it should be made from a material that is resistant to alcohol, such as a woven cloth or a resin film. When the bag is formed from a woven cloth, the gaps in the weave serve as the liquid passage holes, so there is no need to make any liquid passage holes, but when the bag is formed from a resin film, liquid passage holes must be made in the film at the desired pitch.

Examples of the narrow passage used in the manufacturing method in claim 2 include a column, and a section in which plates are set up in parallel at the desired spacing. The diameter of the column or the spacing of the plates should be set so as to maximize the contact efficiency with the adsorbent during liquid passage.

There are no particular restrictions on the adsorbent that has no limonoid glucoside adsorptivity but is capable of removing impurity coloring components, unpleasant odor components, and unwanted flavor components, but examples of adsorbents used for decoloration include coal-based activated carbon (such as Kuricol WG460 made by Kurita Kogyo) and lignite-based activated carbon (such as Kuricol WG490 made by Kurita Kogyo), and examples of those used for deodorization include wood-based activated carbon (such as Kuricol WG491 made by Kurita Kogyo).

There are no particular restrictions on the method by which the impurity coloring components, unpleasant odor components, and unwanted flavor components in the liquid containing the limonoid glucosides are brought into contact with these adsorbents, but examples include column and batch methods commonly employed in the past.

The following ranges are preferable for the conditions of treatment with super-critical carbon dioxide in the manufacturing method in claim 3.

Treatment pressure: 72.8 kg/cm$^2$ (critical pressure) to 500 kg/cm$^2$, and preferably 200 to 400 kg/cm$^2$ Treatment temperature: 31.1° C. (critical temperature) to 100° C., and preferably 35° to 55° C.

Treatment time: 5 to 60 minutes, and preferably 10 to 20 minutes

Specifically, if the treatment pressure is too low, there is the danger that the expected refining efficiency will not be realized because of the low extraction efficiency of the super-critical carbon dioxide, and while the extraction efficiency will increase if the pressure is high, if it is too high, this will pose practical difficulties because of problems with the mechanical equipment (eg, it must be pressure resistant).

Meanwhile, if the treatment temperature is too low, there is the danger that the expected refining efficiency will not be realized because of the low extraction efficiency of the super-critical carbon dioxide, and while the extraction efficiency will increase if the pressure is high, if it is too high, this will pose practical difficulties because of problems with the mechanical equipment, and there is also the danger that the quality of the limonoid glucosides themselves will be affected.

If the treatment time is too short, the refining effected by the super-critical carbon dioxide will be inadequate. With a batch method, efficiency basically increases along with treatment time, although it is also affected by the amount of super-critical carbon dioxide. However, there is the danger that practical problems will be encountered if the time is too long.

The limonoid glucoside content in the glucoside-containing liquid obtained as above can be adjusted as dictated by the intended application. Also, the limonoid glucoside-containing liquid is used in the form of an alcohol solution, an aqueous solution, or the like as dictated by the intended application.

Furthermore, the individual limonoid glucosides can be isolated from the limonoid glucoside-containing liquid by separation chromatography or another such fractionation method.

PREFERRED EMBODIMENTS OF THE INVENTION

Preferred embodiments of the invention will now be described in detail through reference to the figures. First, the steps in the first method will be described in detail through the use of FIG. 1.

1) An adsorbent 1 is put into a bag 2 having openings that are smaller than the particle diameter of the adsorbent 1, and this bag 2 is immersed in a treatment tank 3.

2) Juice, molasses, or another raw material is supplied as the treatment liquid 4 from a supply port 31 at the top to the inside of the treatment tank 3, and is discharged from a discharge port 32 at the bottom in an amount equal to the supplied amount. Specifically, with this method, the treatment tank 3 is used as the flow passage, and the limonoid glucosides in the treatment liquid 4 are adsorbed to the adsorbent 1 contained in the bag 2 immersed in this treatment tank 3 (flow passage).

3) After the treatment liquid 4 has passed through the treatment tank 3 for a specific length of time, the bag 2 is taken out of the treatment tank 3, and the treatment liquid 4 inside the bag 2 is discharged.

4) The bag 2 is immersed in a water tank and washed.

5) The adsorbent 1 is taken out of the water tank and drained, after which it is immersed in a solvent tank (not shown) filed with ethanol or another organic solvent, which results in the limonoid glucosides that had adhered to the adsorbent 1 being eluted to the organic solvent side to yield a limonoid glucoside-containing liquid.

6) After the limonoid glucoside-containing liquid has been obtained, the adsorbent is taken out of the limonoid glucoside-containing liquid and washed with water, after which it is put back into the bag 2, and steps 1 through 5 are performed.

7) If needed, the limonoid glucoside-containing liquid is refined by adding to the limonoid glucoside-containing liquid an adsorbent such as activated carbon that has no limonoid glucoside adsorptivity but is capable of removing impurity coloring components, unpleasant odor components, and unwanted flavor components. Alternatively, a super-critical carbon dioxide treatment is performed to remove any unpleasant odor components and unwanted flavor components and refine the limonoid glucoside-containing liquid.

This method has outstanding merits as indicated by (a) through (d) below.

(a) Since limonoid glucosides are obtained from juice or molasses, which contain large amounts of limonoid glucosides, they can be obtained more simply and efficiently than with a method for obtaining limonoid glucosides from strained pulp.

(b) Since the bag 2 containing the adsorbent 1 is placed along the flow passage, there is no need for the treatment liquid 4 to be filtered or centrifuged ahead of time. Specifically, the juice, molasses, etc., that is used for the treatment liquid 4 often contains large amounts of impurity solids, and if a treatment liquid 4 that thus contains a large amount of impurity solids is passed through a flow passage such as a column that is tightly packed with an adsorbent, there is the danger that the column will become clogged. However, as mentioned above, a gap is maintained around the bag 2 containing the adsorbent 1 if the bag 2 is installed along the flow passage. Consequently, there will be no clogging when such a treatment liquid 4 containing a large amount of impurity solids is passed directly through the flow passage, which makes continuous operation possible.

(c) The adsorbed limonoid glucosides are eluted into a solvent, after which the adsorbent can be reused merely by being washed with water, so the operation is very simple. Specifically, a regeneration treatment with an alkali is usually required after treatment when adsorption is performed with a synthetic adsorption resin, but when a regeneration treatment with an alkali is performed, not only are a great deal of time and labor required by water washing and the like in order to remove the alkali component, but there is also the danger that a corresponding amount of limonoid glucoside (the adsorbate) will be lost during regeneration. However, if the limonoid glucoside is eluted by an alcohol-based solvent, the resin is at that point continuously restored to a state that permits limonoid glucoside adsorption. Accordingly, the juice, etc., can be treated immediately after going through a short water washing treatment upon completion of the elution treatment. Also, if this adsorption/elution cycle is carried out repeatedly, any limonoid glucosides that had been lost up to now during resin regeneration with an alkali can be recovered efficiently, which dramatically boosts the yield.

(d) If activated carbon that has no limonoid glucoside adsorptivity but is capable of removing impurity coloring components, unpleasant odor components, and unwanted flavor components (such as acridity) is added to the limonoid glucoside-containing liquid thus obtained, then any impurity coloring components, unpleasant odor components, and unwanted flavor components in the resulting limonoid glucoside-containing liquid can be removed. Specifically, the limonoid glucoside-containing liquid obtained by the above method in most cases has a blackish-brown color and has an unpleasant aroma of fruit peel, and this operation allows a limonoid glucoside-containing liquid to be obtained without the unwanted brown pigment or unpleasant odor. Also, unpleasant odor components and unwanted flavor components can be removed if super-critical carbon dioxide is blown into the resulting limonoid glucoside-containing liquid.

The second method will now be described in detail through the use of FIGS. 2 and 3. With the second method, limonoid glucosides can be manufactured by following the steps below.

Figure 2:
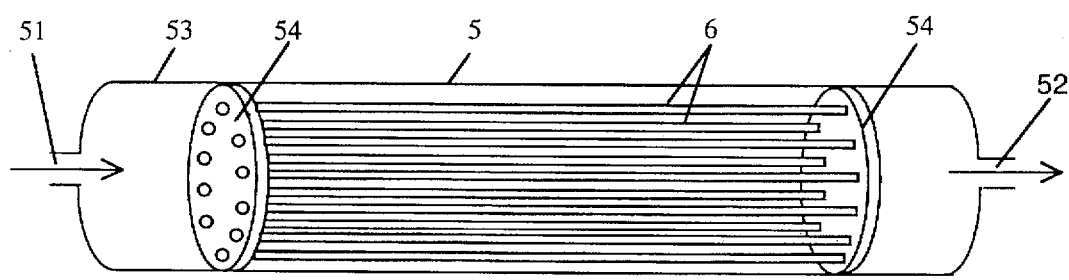
FIG. 2 is a diagram of the limonoid glucoside adsorption module used in the limonoid glucoside manufacturing method pertaining to the present invention.
Figure 3:
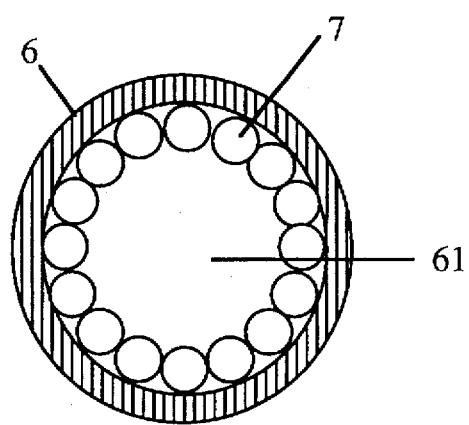
FIG. 3 is a cross section of the column portion of FIG. 2.

(1) A limonoid glucoside adsorption module (hereinafter referred to as "module") 5 is formed as shown in FIG. 2 as the flow passage, and juice or molasses containing a large amount of limonoid glucosides is passed as the treatment liquid at a specific rate through this module 5. The module 5 comprises a unit housing 53, which is equipped with a liquid inflow port 51 at one end and a liquid discharge port 52 at the other end, and numerous columns 6. The unit housing 53 is divided in three by two divider walls 54. The numerous columns 6 are fitted into fitting holes made in the divider walls 54, and are supported at the ends by the divider walls 54. As shown in FIG. 3, the columns 6 have an adsorbent 7 bonded integrally around their inner walls. Specifically, the treatment liquid enters the unit housing 53 from the liquid inflow port 51, passes through the columns, and is discharged from the liquid discharge port 52, and the limonoid glucosides in the treatment liquid are adsorbed inside the columns 6 by the adsorbent 7 on the inner walls of the columns 6.

(2) A specific amount of treatment liquid flows into the module 5, after which the inside of the module 5 is washer with water.

(3) The solvent capable of dissolving limonoid glucosides is passed through the module 5 and the limonoid glucosides adhering to the adsorbent are eluted.

The rest of the procedure is the same as in the second method.

With this method, the adsorbent 7 is integrally bonded to the inner walls of the column 6, so a gap 61 is always maintained in the center of the column, which means that even if the impurity solids in the treatment liquid are not removed ahead of time by filtration or centrifugation, the operation can still be carried out continuously without any clogging occurring.

EXAMPLES

The present invention will now be described in detail through reference to examples thereof.

Example 1

Using concentrated Unshu mandarin juice as the limonoid glucoside recovery source, a limonoid glucoside recovery test was conducted as follows.

⅙ concentrated Unshu mandarin juice was diluted with water and then centrifuged or filtered. The treatment liquid was passed through a column (25 cm$\phi$×120 cm) packed with a styrene DVB-based synthetic adsorbent (XAD-2 made by Organo), and the limonoid glucosides were adsorbed by the synthetic adsorbent.

Next, the column was washed with 100 liters of water, after which the limonoid glucosides were eluted with 15 liters of methanol. The methanol eluate thus obtained was put under reduced pressure to remove the methanol and concentrate the liquid, after which this concentrate was mixed with water to about Bx. 10, and then passed through a column (18 cm$\phi$×100 cm) packed with coconut shell activated charcoal (chromatograph-use activated carbon with an average particle diameter of 180 µm made by Wako Pure Chemical).

After this, the column was washed with 50 liters of water, after which the limonoid glucosides that had adsorbed to the activated charcoal was again eluted with 15 liters of a 50% ethanol aqueous solution, which yielded a limonoid glucoside-containing liquid with a high degree of refinement.

This limonoid glucoside-containing liquid was then passed through a column (15 cm$\phi$×50 cm) packed with an anion exchange resin (DEAE Toyopearl 650C by Tosoh) in order to raise the degree of refinement, after which the limonoid glucosides that had adsorbed to the anion exchange resin were eluted with a 10-liter 0.2M sodium chloride (pH 2.5) solution, after which this product was subjected to a desalting operation, which yielded a high-purity limonoid glucoside-containing liquid.

Example 2

100 kg of natural natsudaidai juice (containing 35 g of limonoid glucosides) was passed through a column packed with 54 liters of a styrene DVB-based synthetic adsorbent (HP-20, made by Mitsubishi Kasei), and the limonoid glucosides were adsorbed to the synthetic adsorbent. The column was washed with water to remove the impurities, after which the limonoid glucosides were eluted from the adsorbent with 100 liters of methanol. Next, this eluate was concentrated under reduced pressure, which yielded a high-purity limonoid glucoside-containing liquid containing 28 g of limonoid glucosides.

Example 3

12 tons of concentrated Valencia orange juice (containing 6.8 kg of limonoid glucosides) was passed through a column packed with 100 liters of a styrene DVB-based synthetic adsorbent (HP-20, made by Mitsubishi Kasei), and [the column] was washed with water to remove the sugars and other such impurities, after which the limonoid glucosides were eluted from the adsorbent with 75% ethanol, which yielded a limonoid glucoside-containing liquid. The limonoid glucoside-containing liquid thus obtained contained 4.6 kg of limonoid glucosides.

Example 4

A stainless steel tank was installed as the treatment tank shown in FIG. 1 in an in-line juicing process, and this tank was filled with freshly squeezed Unshu mandarin juice, after which a 300-mesh bag packed with 2 liters of a styrene DVB-based synthetic adsorbent (XAD-2) made by Organo) was put into the stainless steel tank. Juice was poured in from the upper portion of the tank at a rate of one liter per minute, and juice was discharged at the same rate from the lower portion of the tank. One hour later, the bag was taken out of the tank along with the synthetic adsorbent, and the juice was discharged from inside the bag, after which [the bag] was transferred to a tank filled with 10 liters of water and washed for 10 minutes in this water. The bag was then taken out of the water tank and drained, after which it was immersed for 10 minutes in a tank filled with 10 liters of 75% ethanol to elute the limonoid glucosides. The above operation was repeated five times, after which the 10 liters of eluate thus obtained was concentrated under reduced pressure, which yielded 1 liter of limonoid glucoside-containing liquid that contained 50 g of limonoid glucosides.

Example 5

A total of 3 g of dried styrene DVB-based synthetic adsorbent (XAD-2, made by Organo) was applied around the inner walls of a glass tube with an inside diameter of 5 mm and a length of 500 mm, and 10 similarly prepared glass tubes were brought together to produce a limonoid glucoside adsorption module as shown in FIG. 2. 5 liters of Unshu mandarin juice was then passed through this module at a rate of 100 milliliters per minute, after which the inside of the module was washed with water. 200 milliliters of 55% ethanol was passed through the module to elute the limonoid glucosides that had adsorbed to the adsorbent. The eluate thus obtained was concentrated under reduced pressure, which yielded 10 mL of limonoid glucoside-containing liquid that contained 360 mg of limonoid glucosides.

Example 6

Secondary squeezed juice from Unshu mandarins (hereinafter referred to as "peel water") or a concentrate thereof (molasses) was diluted with water and then centrifuged or filtered to remove the impurity solids. The filtrate was passed through a column (25 cmφ×120 cm) packed with a styrene DVB-based synthetic adsorbent (XAD-2, made by Organo) to adsorb the limonoid glucosides. The inside of the column was washed with 450 liters of water, after which 113 liters of methanol was passed through the column to elute the limonoid glucosides that had adsorbed to the adsorbent. The eluate obtained in this manner was concentrated under reduced pressure to remove the methanol, and this concentrate was mixed with water to about Bx. 10 and passed through a column (18 cmφ×100 cm) packed with activated carbon. The inside of the column was then washed with 150 liters of water, after which 20 liters of 50% ethanol was passed through the column to adsorb the limonoid glucosides that had adsorbed to the activated carbon, which yielded a limonoid glucoside-containing liquid with a high degree of refinement.

This limonoid glucoside-containing liquid was then passed through a column (15 cmφ×50 cm) packed with an anion exchange resin (DEAE Toyopearl 650C by Tosoh) in order to raise the degree of refinement, after which the limonoid glucosides that had adsorbed to the anion exchange resin were eluted with a 10-liter 0.2M sodium chloride (pH 2.5) solution, after which this product was subjected to a desalting operation, which yielded a high-purity limonoid glucoside-containing liquid.

Example 7

100 kg of peel water (containing 133 g of limonoid glucosides) was passed through a column packed with 54 liters of a styrene DVB-based synthetic adsorbent (HP-20, made by Mitsubishi Kasei), and the limonoid glucosides were adsorbed to the synthetic adsorbent. The column was washed with water to remove the impurities, after which the limonoid glucosides were eluted from the adsorbent with 100 liters of methanol. Next, this eluate was concentrated under reduced pressure, which yielded a high-purity limonoid glucoside-containing liquid containing 110 g of limonoid glucosides.

Example 8

Peel water containing 75 g of limonoid glucosides was passed through an activated carbon column (packed with 4 kg of chromatograph-use activated carbon, made by Wako Pure Chemical). The column was washed with water, after which 20 liters of 50% ethanol was passed through the column to elute the limonoid glucosides that had adsorbed to the activated carbon. This eluate was concentrated under reduced pressure, which yielded 1 liter of limonoid glucoside-containing liquid containing 53 g of limonoid glucosides.

Example 9

One liter of each of the limonoid glucoside-containing liquids obtained in Examples 1 through 8 was passed first through a column packed with 100 g of decoloration-use activated carbon (Kuricol WG-460, made by Kurita Kogyo) and then through a column packed with 100 g of deodorization-use activated carbon (Kuricol WG-491, made by Kurita Kogyo). As a result, the remaining brown coloring, unpleasant odor, and acrid taste were completely removed from all of the limonoid glucoside-containing liquids obtained in Examples 1 through 8. Also, the limonoid glucosides did not adsorb to the column at this time, and a recovery rate of nearly 100% was achieved.

Example 10

20 milliliters of each of the limonoid glucoside-containing liquids obtained in Examples 1 through 8 was sampled into the extraction tank (internal volume: 50 cm$^3$) of a super-critical carbon dioxide extraction apparatus (Super-200, made by Nihon Bunkosha), and super-critical carbon dioxide was supplied for 20 minutes at a rate of 4 g per minute at 40° C. and 300 kg/cm$^2$ to remove the unpleasant odor component and unwanted flavor component. As a result, the remaining unpleasant odor and acrid taste were completely removed from all of the limonoid glucoside-containing liquids obtained in Examples 1 through 8. Furthermore, the limonoid glucosides were not removed at all, with 100% remaining in the treatment liquid.

We claim:

1. A method for manufacturing limonoid glucosides, comprising a step in which a raw material composed of citrus juice and/or molasses is passed through a flow passage equipped with an adsorbent having limonoid glucoside adsorptivity, after which the limonoid glucosides that have been adsorbed by the adsorbent in the flow passage are eluted into a solvent by means of a solvent capable of dissolving the limonoid glucosides, which yields a liquid containing limonoid glucosides, wherein the adsorbent having limonoid glucoside adsorptivity is put into a bag having numerous liquid passage holes with a diameter smaller than the particle diameter of the adsorbent, and this bag is placed along the flow passage.

2. A method for manufacturing limonoid glucosides, comprising a step in which a raw material composed of citrus juice and/or molasses is passed through a flow passage equipped with an adsorbent having limonoid glucoside adsorptivity, after which the limonoid glucosides that have been adsorbed by the adsorbent in the flow passage are eluted into a solvent by means of a solvent capable of dissolving the limonoid glucosides, which yields a liquid containing limonoid glucosides, wherein citrus juice or molasses thereof is passed through a flow passage at least part of which has been formed into a narrow passage in which an adsorbent having limonoid glucoside adsorptivity has been bonded and integrated along the inner walls.

3. A method for manufacturing limonoid glucosides, comprising a refining step in which super-critical carbon dioxide is supplied under pressure to a liquid containing limonoid glucosides obtained by any of the manufacturing methods in claims 1 or 2, and unpleasant odor components and unwanted flavor components are thereby removed.

* * * * *